United States Patent [19]
Farzin-Nia et al.

[11] Patent Number: 5,219,283
[45] Date of Patent: Jun. 15, 1993

[54] ORTHODONTIC BRACKET, METHOD OF MAKING AN ORTHODONTIC BRACKET, AND METHOD OF APPLYING AN ORTHODONTIC BRACKET TO THE TOOTH

[75] Inventors: Farrokh Farzin-Nia, Inglewood; Raymond F. Wong, Chino; Terry L. Sterrett, Long Beach, all of Calif.

[73] Assignee: Ormco Corporation, Glendora, Calif.

[21] Appl. No.: 781,679

[22] Filed: Oct. 24, 1991

Related U.S. Application Data

[63] Continuation of Ser. No. 413,620, Sep. 28, 1989, abandoned.

[51] Int. Cl.⁵ .............................................. A61C 3/00
[52] U.S. Cl. .................................................... 433/9
[58] Field of Search .................................... 433/8, 9

[56] References Cited

U.S. PATENT DOCUMENTS

| | | | |
|---|---|---|---|
| 3,955,282 | 5/1976 | McNall | 433/9 |
| 3,975,824 | 8/1976 | Lee | 433/14 |
| 4,050,156 | 9/1977 | Chasanoff et al. | 433/8 |
| 4,165,561 | 8/1979 | Miller et al. | 433/9 |
| 4,200,980 | 5/1980 | Johnston | 433/9 |
| 4,216,583 | 8/1980 | Reynolds | 433/9 |
| 4,340,529 | 7/1982 | Lee, Jr. et al. | 433/9 |
| 4,380,432 | 4/1983 | Orlowski et al. | 433/9 |
| 4,460,336 | 7/1984 | Smith et al. | 433/9 |
| 4,595,598 | 6/1986 | De Luca et al. | 433/8 |
| 4,600,383 | 7/1986 | Smith et al. | 433/9 |
| 4,604,057 | 8/1986 | Viglietti | 433/9 |
| 4,626,209 | 12/1986 | Tsai et al. | 433/9 |
| 4,639,218 | 1/1987 | Jones et al. | 433/8 |
| 4,661,059 | 4/1987 | Kanno | 433/9 |
| 4,681,538 | 7/1987 | De Luca et al. | 433/9 |
| 4,752,221 | 6/1988 | Hanson et al. | 433/9 |
| 4,784,606 | 11/1988 | Jones et al. | 433/8 |
| 4,826,430 | 5/1989 | Chen et al. | 433/8 |
| 4,948,366 | 8/1990 | Horn et al. | 433/8 |

FOREIGN PATENT DOCUMENTS

| | | | |
|---|---|---|---|
| 0099741 | 2/1984 | European Pat. Off. | 433/9 |
| 2563426 | 10/1985 | France | 433/9 |

OTHER PUBLICATIONS

Gem Bracket by Ormco.
"A Comparison with Foil Mesh" by Dr. Hansen, American Journal of Orthodontics, vol. 83, No. 1, Jan. 1983.
Unitek/3M Brochure—Mechanical Retention, "We added something familiar to our ceramic brackets".

*Primary Examiner*—Cary E. O'Connor
*Attorney, Agent, or Firm*—Wood, Herron & Evans

[57] ABSTRACT

In one aspect of the present invention, it is provided an orthodontic bracket having a base portion for attachment to a tooth. The base portion is provided with a substantially monolayer of substantially uniform size particles. The particles are secured to the bonding base through the use of an adhesive.

In another aspect, there is provided a method of making an orthodontic bracket having a bonding base for attachment to the surface of a tooth, comprising the steps of:
(a) applying a curable adhesive layer to the bonding base;
(b) applying a substantially monolayer of particles of substantially uniform size to the bonding base; and
(c) curing the adhesive so as to bond the particles to the bonding surface.

In yet another aspect there is provided an orthodontic bracket having a bonding base for attachment to the surface of a tooth. The bonding base having means for minimizing removal of enamel from the tooth during removal of the bonded bracket from the tooth.

24 Claims, 4 Drawing Sheets

ORTHODONTIC BRACKET, METHOD OF MAKING AN ORTHODONTIC BRACKET, AND METHOD OF APPLYING AN ORTHODONTIC BRACKET TO THE TOOTH

This is a continuation of application Ser. No. 07/413,620, filed Sep. 28, 1989, now abandoned.

BACKGROUND OF THE INVENTION

The present invention relates to orthodontic brackets, and more particularly, an orthodontic bracket having an improved bonding base, and a method for making same.

In the practice of orthodontia, orthodontic brackets are typically bonded directly to the teeth of a patient. It has always been important to provide good bonding between the orthodontic bracket and the tooth. Over the years, many improvements have been made to metal orthodontic brackets and the adhesive used to bond the metal brackets to the teeth. As a result, the bonding of typical prior art metal brackets to the teeth has reached generally accepted values. Recently, aesthetic brackets have become extremely popular. Typically, these aesthetic brackets are made of materials other than metal, and typically are substantially transparent, or tooth-like in color. For example, recently, orthodontic brackets made out of single crystalline material and strengthened glass have been suggested. While these new materials have offered many possibilities in providing brackets with an aesthetically pleasing appearance, the task of bonding these brackets to the tooth has become much more complicated. Due to the hard smooth surface condition of these materials, it is substantially more difficult to provide a high strength bond between the bracket and the tooth. One method of improving the bonding strength between a bracket made of single crystal alumina and a tooth is suggested in U.S. Pat. No. 4,681,538. However, the method disclosed in this patent requires special handling and care in order to obtain acceptable bonding strength. Additionally, a serious problem with such chemically treated adhesion systems of the prior art is that when these brackets are removed or broken from the tooth, there is a high risk that a portion of the tooth enamel will also be removed.

It has also been suggested in the prior art the provision of undercuts on the base of crystalline or ceramic brackets. While such undercuts have improved bonding strengths, these undercuts do not provide the same strength typically found with prior art metal brackets. Another problem encountered with adhesives for aesthetic brackets is that certain adhesives have been found to detract from the transparent or translucent characteristics of the bracket.

It has also been suggested that the application of a substantially monolayer of particles of substantially uniform size to the bonding base of an orthodontic bracket as set forth in Applicant's copending patent application, Ser. No. 241,193, filed Sep. 7, 1988. While this has proven satisfactory in providing desired bond strengths, the method employed requires the brackets to be heated to high temperatures so as to diffusion bond the particles to the bracket. This heating process requires time and adds further cost to the product. Additionally, diffusion does not work well for materials such as glass, as it tends to damage the particles and/or the bracket during the heating process.

Applicant has invented an improved orthodontic bracket and method of making same wherein acceptable bonding strengths are obtained while maintaining the attractive aesthetic qualities of the bracket and additionally minimizes the possibility of removing enamel from the tooth.

SUMMARY OF THE INVENTION

In one aspect of the present invention, it is provided an orthodontic bracket having a base portion for attachment to a tooth. The base portion is provided with a substantially monolayer of substantially uniform size particles. The particles are secured to the bonding base through the use of an adhesive.

In another aspect, there is provided a method of making an orthodontic bracket having a bonding base for attachment to the surface of a tooth, comprising the steps of:

(a) applying a curable adhesive layer to the bonding base;

(b) applying a substantially monolayer of substantially uniform size particles to the bonding base; and (c) curing said adhesive so as to bond the particles to the bonding surface.

In yet another aspect there is provided an orthodontic bracket having a bonding base for attachment to the surface of a tooth. The bonding base having means for minimizing removal of enamel from the tooth during removal of the bonded bracket from the tooth.

DETAILED DESCRIPTION OF THE DRAWINGS

DETAILED DESCRIPTION

Figure 1:
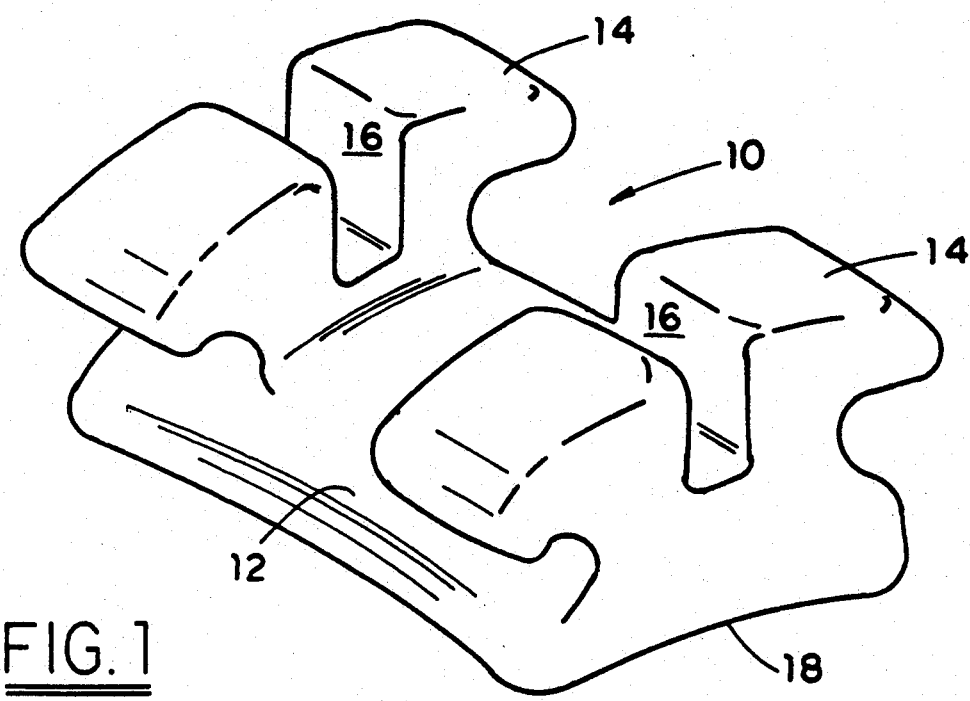
FIG. 1 is a perspective view of an orthodontic bracket made in accordance with the present invention.
Figure 2:
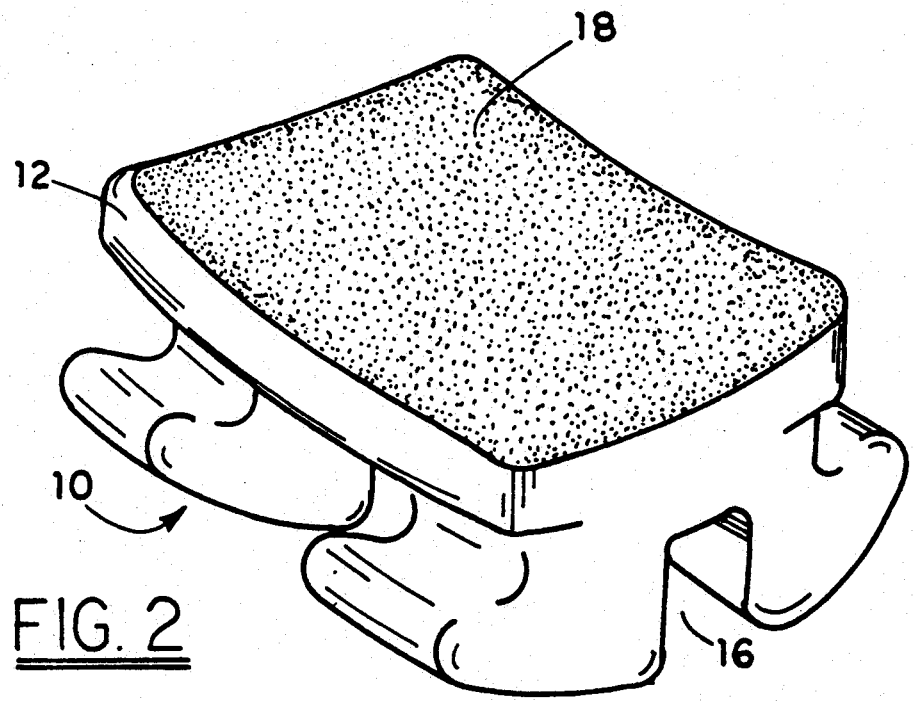
FIG. 2 is a bottom perspective view of the orthodontic bracket of FIG. 1.
Figure 3:
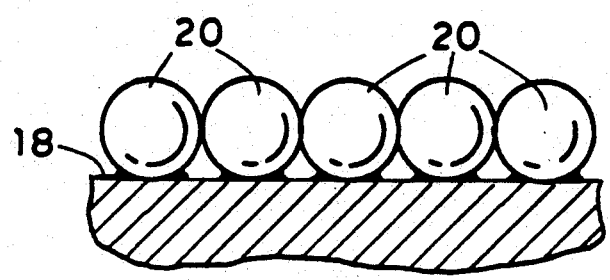
FIG. 3 is a greatly enlarged partial side elevational view of the bonding base of the bracket of FIG. 1.
Figure 4:
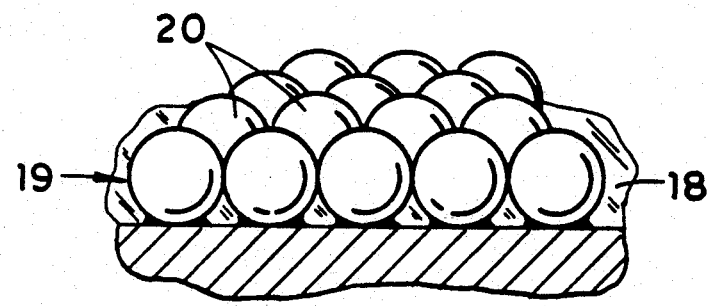
FIG. 4 is a perspective view of the bonding base of FIG. 3.

Referring to FIGS. 1-4, there is illustrated an orthodontic bracket 10 made in accordance with the present invention. The bracket 10 is designed to be attached directly to the tooth of a patient as is customarily done in the prior art. The orthodontic bracket 10 comprises a base portion 12 and a pair of tie wings 14 which extend from the base portion 12. Tie wings 14 are each provided with an elongated slot 16 for receiving an orthodontic archwire (not shown) as is customarily done in the prior art. In the particular embodiment illustrated, the orthodontic bracket 10 is made of a glass material (amorphous or crystalline). However, the bracket 10 may be made out of other suitable materials, for example, ceramics, crystalline and metal. The orthodontic bracket 10 in the embodiment illustrated is made out of a transformation-toughened glass material. A suitable glass composition for bracket 10 is as follows:

| MATERIAL | PERCENTAGE (By Weight) |
| --- | --- |
| $SiO_2$ | 58.8 |
| $Al_2O_3$ | 18.5 |
| $ZnO$ | 12.5 |
| $Li_2O$ | 5.3 |
| $Na_2O$ | 3.3 |
| $Sb_2O_3$ | 1.5 |
| $K_2O$ | .1 |

It is to be understood that various other glass or ceramic compositions may be used, for example, such as set forth and described in copending U.S. application Ser. No. 07/53875, filed May 26, 1989. This copending application is hereby incorporated by reference into this application.

Base 12 of bracket 10 has a tooth contact surface 18 for placement against the surface of a tooth of a patient. Surface 18 is provided with a substantially monolayer 19 of individual particles 20 as illustrated (see FIGS. 3, 4 and 5). The particles 20 are of substantially uniform size and have a size in the range of about 5 microns to about 200 microns. The size variation in the layer is such that small particles do not completely fill the voids that exist between adjacent particles 20. Preferably the size variation of particles in layer 19 is such that the smaller particles are not less than about 75% in size of the layer particles, most preferably not less than about 85%. Applicant has found that the particle 20 are preferably spherical in shape, and preferably have a size in the range of about 40-70 microns. In the preferred embodiment, particles 20 are made of the same or similar material as base 12. In the particular embodiment illustrated, pure silica hollow spheres are used and purchased from Emerson and Cuming of Canton, Mass. and identified as SI type microballoon.

Since base 12 and particles 20 are made of glass in the embodiment illustrated, it is desirable to enhance or promote adhesion between particle 20 and surface 18. One way to accomplish this is by roughening the surface 18 of base 12. In the particular embodiment illustrated, the bonding base surface 18 is etched with a solution of hydrofluoric acid. In particular, a solution containing three parts 48% hydrofluoric acid and one part 85% $H_3PO_4$ is used to roughen the surface 18. The solution is applied to the surface 18 for a predetermined time period. Applicant has found that a time period of approximately in the range of about 30-60 seconds at room temperature is sufficient. At the end of this time period, the base is rinsed with a deionized water for approximately 1 minute. The bracket 10 is then allowed to dry. In the preferred embodiment, the bracket 10 is dried at about 100° C. for about 1 hour to assure that all moisture has been removed.

Adhesion between particles 20 and surface 18 may also be enhanced through the application of an adhesive promoting solution. In the particular embodiment illustrated, a silane adhesive promoting solution is next applied on the bracket. Applicant has found that a silane solution sold by Union Carbide, under the brandname A-174, works very satisfactorily. The bracket is appropriately coated by either dipping the entire bracket 10 within the solution or spraying the solution on the base 18. After the solution has been applied, it is appropriately dried. Applicant has found that exposing the bracket 10 at a temperature of about 110° C. for approximately 1 hour is sufficient for drying the bracket 10. In the preferred embodiment described, the surface 18 is roughened and treated with an appropriate adhesion enhancement solution as described, however, it is to be understood that only a single enhancement may be used as described or other suitable treatments may be used as desired or required by the material being used.

An adhesive resin is then applied onto the bonding base surface 18, preferably a light-curable unfilled adhesive. A sufficient amount of the adhesive is applied so as to provide a thin layer, preferably having a thickness in the range of about 0.001 to 0.002 inches. The adhesive layer is partially cured so as to render the adhesive tacky. In the particular embodiment illustrated, this is accomplished via a 10 second exposure of the adhesive to a light source capable of curing the adhesive. In the particular embodiment illustrated, the adhesive is IC2105 produced by Scipharm which comprises a low viscosity dimethacrylate sealant. However, it is to be understood that any other adhesive having the desired strength properties may be used. Additionally, while the use of a light adhesive is taught, other types of adhesives may be used and other methods for partially curing adhesive may be employed. All that is important is at this point in time is that the adhesive, prior to the applying of the particles 20 onto surface 18, be tacky so as to allow the particles 20 to adhere thereon in a firm manner during further processing until final curing of the adhesive can take place. Applicant has found that a light cure adhesive provides a number of advantages in its use, for example, ease and control of particle curing so as to be partially cured which renders the adhesive tacky.

The particles 20 are then applied to the bonding surface 18. In the preferred embodiment illustrated, the particles 20 comprise hollow glass spheres, however, solid spherical particles may be used if desired. Hollow glass spheres are preferred over solid glass spheres in that they assist in providing a weakened area designed to fail prior to removing enamel from the tooth so as to minimize or prevent enamel damage from being removed from the tooth. However, solid glass spheres or irregular shaped particles may be used if desired.

In the particular embodiment illustrated, the glass spheres applied to surface 18 may, if desired, be treated with an adhesive promoting silane solution in the same manner previously discussed with the surface 18. The bracket 10 is then placed in a container filled with the glass spheres and moved around until the surface 18 is filled with a substantially monolayer of spheres on surface 18. Since the adhesive is tacky, the spheres will be maintained on surface 18 with a sufficient force so that they will not move under normal manufacturing conditions. The bracket is then removed from the container and any excess particles 20 are easily shaken off.

The adhesive layer is then fully cured. In the particular embodiment illustrated, this is accomplished by simply exposing the adhesive layer to an appropriate light source, for example, as previously conducted for particle curing, for an appropriate period of time for fully curing the adhesive. In the particular embodiment illustrated, twenty (20) seconds under a Dynamax ultraviolet light has been found to be a sufficient time period to fully cure the adhesive layer. However, it is to be understood that the time period required may be varied as appropriate in accordance with the adhesive system being used.

The bracket 10 is then bonded to the tooth as is customarily done in the prior art. First, an adhesive is applied to bonding base 18 and particle 20 and the bracket is then applied to the surface of the tooth as is customarily done.

Figure 5:
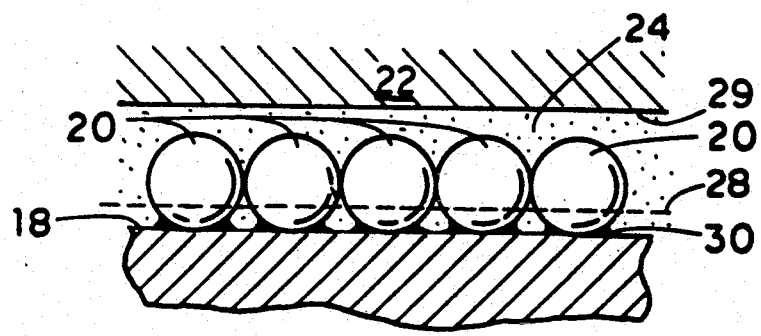
FIG. 5 is an exploded side view of the bracket of FIG. 3 shown adjacent the tooth.

Referring to FIG. 5, there is illustrated a greatly enlarged view of a portion of the bracket 10 as bonded to a tooth 22 illustrating the particles 20 embedded in the adhesive 24 used to bond the bracket 10 to the tooth 22. The adhesive 24 may be any suitable adhesive as is typically used. In the particular embodiment illustrated, adhesive 24 is typically used. In the particular embodiment illustrated, adhesive 24 is a filled adhesive sold under the trademark Concise by the 3M Corporation. The use of a bonding system that utilizes a substantially monolayer of particles of substantially uniform size adhesively bonded to the base and adhesives for bonding the bracket 10 to the tooth 22 produces a system that yields a fracture plane 28 between the bracket and tooth to occur away from the bond between the tooth 22 and adhesive 24. Thus, when the bracket is to be removed or an excess amount of force is applied to the bracket 10, rupture of the bond will occur at a fracture plane 28 closest to the bonding base 12 away from the tooth adhesive joint 29. Typically, the fracture plane 28 will be between the mid point of the particles 20 and surface of the base 12. Various factors previously discussed may be varied so to control the amount of force necessary to cause failure of the bond between the bracket 10 and tooth 22 and still keep the fracture plane 28 away from the tooth/adhesive joint. Preferably, as in the embodiment illustrated, the adhesive used to bond the particles 20 to base 12 is less than the bond strength of the adhesive used to bond the bracket to the tooth 22. In addition to controlling the type of adhesive used, the amount of adhesive used to bond particles 20 to base 12, the less amount used will generally cause failure of the bond at lower forces. In the particular embodiment illustrated, the adhesives used to bond particles 20 to base 12 form a relatively small collar 30 around the particles. As more adhesive is applied, the greater the bond strength between the particles 20 and base 12 until reaching a maximum value and will then decrease. Failure of the bond between the bracket 10 and tooth 22 can also be affected by the type and size of particles used. Hollow sphere particles, of course, provide an area which allow rupture of the particles. The size, shape and thickness of the walls of the particles 20 also have an effect on the overall bond strength and failure point.

In the preferred embodiment illustrated, the particles 20 and adhesive used provide a bracket/tooth bond that will fail when a force greater than about 30 lbs. is applied to the bracket 10. Typically, the spheres 20 will either rupture or completely come off base 12. In either event, substantially no enamel is removed from the tooth.

The present invention provides a bonding system designed to fail at a location away from the tooth adhesive joint 29 so as to minimize or prevent removal of enamel from the surface of the tooth. The particle 20, as previously discussed, is made of a glass material which has a resistance to abrasion lower than the tooth enamel or other commonly used material such as single or polycrystalline material and ceramics used to make orthodontic brackets and like appliances. By using a relatively low abrasion resistant material for particles 20, any particles 20 remaining on the tooth can be easily removed by the orthodontist without the need for use of diamond tools and damaging the tooth or causing fast wear to the burs.

Figure 6:
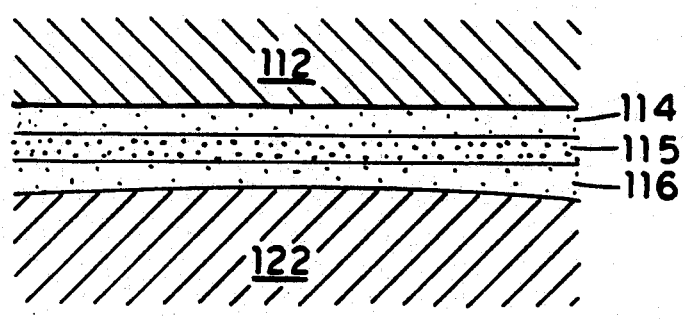
FIG. 6 is an enlarged partial view of a modified bracket made in accordance with the present invention bonded to a tooth.

In the embodiment illustrated in FIGS. 1-5 a portion predetermined fracture plane is provided through the use of a plurality of particles 20 adhered to the bonding base surface. It is to be understood that various other structures may be provided for producing a fracture plane disposed away from the tooth adhesive joint. Referring to FIG. 6, there is illustrated an enlarged front elevational view of a portion of an orthodontic bracket made in accordance with the present invention having a bonding base portion 112 which is adhesively bonded to the tooth 122. In this particular embodiment, a first adhesive layer 114 is provided adjacent to the base portion 112 and is preferably of a filled type adhesive. A second intermediate adhesive layer 115 is provided adjacent to first adhesive layer 114. In the particular embodiment illustrated, intermediate adhesive layer 115 is an unfilled adhesive sealant. An outer adhesive layer 116 is provided between the tooth 122 and intermediate adhesive layer 115. The third adhesive layer is preferably a filled adhesive. In the particular embodiment illustrated, adhesive layers 114 and 116 comprise a layer of light cure filled bonding adhesive, and second adhesive layer 115 is an unfilled light cure sealant and are of type typically available and presently used in the practice of orthodontics. For example, adhesives sold under the trademark Transbond. The adhesive layers 114 and 116 are designed to possess a shear strength greater than that of the intermediate adhesive layer 115. In the particular embodiment illustrated, the adhesive layers 114, 116 can withstand a shear load of approximately 30 pounds, whereas the intermediate layer 115 can resist a shear force of about ten pounds. Thus, when a shear force greater than about 10 pounds is applied, the fracture of the bond between the bracket and tooth will occur at intermediate layer 115. Thus bracket tooth assembly provides a predetermined ruptured plane that is away from the bond joint between the adhesive layer 116 and the surface of the tooth 122.

In the particular embodiment illustrated, the adhesive may be applied is a series of steps. First, adhesive layer 114 is placed on the base portion 112 of the bracket and an adhesive layer 116 is placed on the tooth 122. Both layers 114, 116 are then partially cured by exposing the adhesive layers 114, 116 to a curing lamp for approximately 10 seconds. It is, of course, to be understood that the other adhesive may be used requiring other curing techniques. After layers have been partially cured, sealant intermediate layer 115 is applied either to the tooth 122 or the bonding base 112 over the adjacent partially cured adhesive layer 114. The bracket and the tooth are then brought together and the adhesive layers 114, 115, 116 are completely cured. The resulting bond strength of the bracket to the tooth will exhibit a strength of approximately 10 pounds, i.e. the strength of the weakest element. When the bracket is designed to be removed or is accidentally subjected to excess force, the bond will break at the weakest point, i.e. being between the intermediate layer 115 and the adjacent layers 114 and 116. Thus, minimizing or eliminating the potential of removing enamel from the tooth. It is to be understood that the sandwich adhesive layer structure as set forth in FIG. 6, may be obtained by other method steps. For example, the adhesive layer 114 may be placed on the bonding base portion 112, and thereafter fully cured, in the particular embodiment illustrated by exposing the light cured adhesive to an appropriate light source. Thereafter, the cured adhesive layer could be treated with a methacrylic acid solution (for example, 30% ethanol) for about 30 seconds. Thereafter, a second adhesive layer 116 is placed on the tooth, and the bracket is brought into contact with the adhesive on the tooth and fully cured with the appropriate light source. It is to be further understood that various other type adhesives may be used having the desired sheer strength in each of the respective layers 114, 115, 116 so that a weaker adhesive layer is formed between the bracket and tooth which is away from the tooth adhesive interface.

Figure 7:
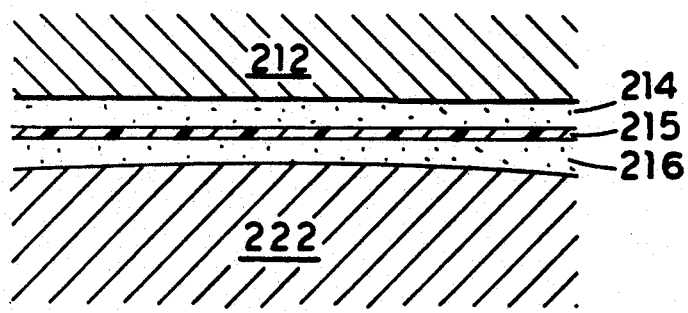
FIG. 7 is an enlarged partial view of yet another modified bracket made in accordance with the present invention bonded to a tooth.

Referring to FIG. 7, there is illustrated yet another embodiment made in accordance with the present invention. In this particular embodiment, there is illustrated a bracket having a bonding portion 212, which is adhered to a tooth 222. A first light curable filled adhesive layer 214, is applied adjacent to the base portion 212. A polyvinylchloride (PVC) plastic film is placed adjacent the filled adhesive layer 114 and a second light curable adhesive layer 216 is placed between the tooth and the plastic barrier film layer 215. Preferably the thin film layer 115 has a thickness in the range of 0.0005 to approximately 0.0015 inches. Examples of suitable materials are; polyurethane, polyethylene, nylon, etc. In order to provide adequate bonding between the film 215 and the adjacent adhesive layers, the surfaces of the film are preferably treated to improve adhesion bonding, for example, chemical grafting, plasma deposition, plasma etching, as is well known in the art. In the particular embodiment illustrated, the barrier film 215 is a plasticized 55 shore D polyvinylchloride plastic. The surfaces are prepared for bonding by etching the surfaces with a solution of one part pvc monomer and 5 parts cyclohexanone, for fifteen seconds. The etched pvc film barrier 215 is placed between conventional adhesive layers 214, 216. In the particular embodiment illustrated, adhesive layers 214, 216 comprise filled light cured adhesive similar to that discussed in the embodiment in FIGS. 1-5.

It is to be understood that various other material may be used for film barrier and surface treated in any other way. For example, urethane films with a chemically grafted methacrylate functionality as sold by Polymer Research Corporation of Brooklyn, N.Y. Alternate grafting methods include plasma deposition of methacrylic acid and the like on the polyurethane surface by plasma deposition as done by Plasma Science Corporation of Belmont, California. Film layer 215 provides a weak point which will fail when excess shear force is applied to the bracket tooth assembly. Since the film provides the weakest link in the assembly, failure will occur at this point away from the adhesive 216 tooth interface.

Figure 8:
FIG. 8 is an enlarged formatting view of still another bracket made in accordance with the present invention bonded to a tooth.
Figure 9:
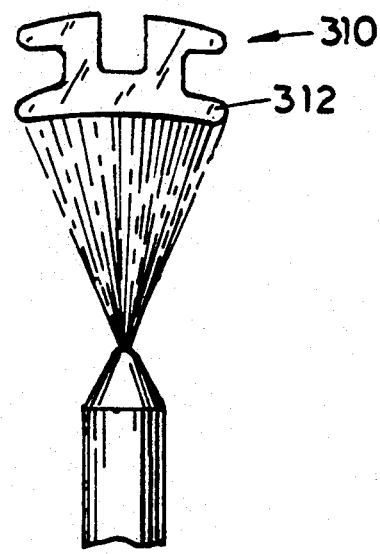
FIG. 9 is a schematic representation illustrating one step in making the bracket of FIG. 8.

Referring to FIG. 8 there is illustrated another enlarged partial elevational view of the base portion 312 of a bracket made in accordance with the present invention bonded to tooth 322. In this particular embodiment, the base portion 312 is provided with a surface preparation that will cause a failure point away from the adhesive tooth joint interface 329. A plurality of crystal structure 315 are grown on the base portion 312. U.S. Pat. No. 4,600,383 is representative of known techniques that can be employed to grow the crystals. In the particular embodiment illustrated in FIG. 9, the bonding base would be initially provided with a layer 314 of hydroxyapitite sprayed on for example by plasma or vacuum deposition. In the particular embodiment illustrated base portion 312 is made out of glass material, similar to that illustrated in FIGS. 1-5. Therefore, in order to grow crystal structure 315 on the base portion 312, it is necessary to prepare the surface which in the particular case requires the plasma spraying of the hydroxyapitite. The outer surface 312 is then prepared with crystal growth solution for bonding. The attachment of the adhesive to the bracket by the way of encapsulation of the crystals formed on the base 312 by the adhesive 316. The crystals 315 serve as the weak link in the bond joint between the bracket and tooth 332. Thus yielding a fracture plane designed to fail prior to failure of the adhesive tooth joint 329.

It is to be understood that various other changes and modifications may be made without departing from the scope of the present invention. For example, but not by way of limitation, the orthodontic bracket may be made out of other hard materials, such as single crystalline materials, ceramics and polycrystalline materials. Additionally, various types of adhesive systems may be used. Still further, the particles may take other uniform or irregular shapes. The scope of the present invention being defined by the following claims.

What is claimed is:

1. A method of making an orthodontic bracket having a bonding base for attachment to the surface of a tooth, comprising the steps of:
   (a) applying a curable adhesive layer to said bonding base;
   (b) applying a substantially monolayer of adjacent particles to said bonding base, said adjacent particles being of substantially uniform size such that small particles do not completely fill the void between adjacent particles; and
   (c) curing said adhesive so as to bond said particles to said bonding surface.

2. A method of making an orthodontic bracket according to claim 1 wherein said bonding base prior to having said adhesive layer applied is subject to an adhesive promotion treatment.

3. A method of making an orthodontic bracket according to claim 2 wherein said bonding base is made of a glass material.

4. A method of making an orthodontic bracket according to claim 2 wherein said bonding base is coated with an adhesive promoting solution.

5. A method of making an orthodontic bracket according to claim 1 wherein said particles prior to being applied to said bonding base is subjected to a adhesive promoting solution.

6. A method of making an orthodontic bracket according to claim 1 wherein said substantially particles are hollow.

7. A method of making an orthodontic bracket according to claim 1 wherein said particles are substantially spherical in shape.

8. A method of making an orthodontic bracket according to claim 1 wherein after said curable adhesive layer is applied to said bonding base and prior to the application of substantially particles, said adhesive layer is partially cured so as to render said adhesive layer tacky to limit the formation of filler by the adhesive around the spheres prior to being fully cured.

9. A method of making an orthodontic bracket according to claim 8 wherein said bracket and spherical particles are made of a glass material.

10. A method of making an orthodontic bracket according to claim 1 wherein said substantial particles are made of the same material as said orthodontic bracket.

11. A method of making an orthodontic bracket having a bonding base for attachment to the surface of a tooth, comprising the steps of:
   (a) applying a light curable adhesive layer to said bonding base;
   (b) partially curing said adhesive layer so as to render said adhesive layer tacky;
   (c) applying a substantially monolayer of adjacent particles to said bonding base, said adjacent particles being of substantially uniform size such that small particles do not completely fill the void between adjacent particles.

12. A method of making an orthodontic bracket according to claim 11 wherein said bonding base is made of a glass material.

13. A method of making an orthodontic bracket according to claim 11 wherein said bonding base is coated with an adhesive promoting solution.

14. A method according to claim 11 wherein said particles prior to being applied to said bending base is subjected to an adhesive promoting solution and allowed to dry.

15. A method according to claim 11 wherein said bonding base prior the application of said light curable adhesive layer is roughened by the application of an etching solution, said etching solution comprising three parts hydrofluoride and one part $H_3PO_4$ and is applied to surface of said bonding base for a time period of about 30-60 seconds at room temperature.

16. A method according to claim 15 where at the end of said time period said etching is rinsed with deionized water for approximately one minute and is dried at 100° C. for approximately one hour.

17. A method according to claim 16 wherein said bracket and said spherical particles are made of a glass material.

18. An orthodontic bracket having a bonding base for attachment to the surface of a tooth, said bonding base having a substantially monolayer of particles adhesively bonded thereto, said particles being made of substantially the same material as said bracket, said particles being hollow so that they rupture during removal of said bracket from said tooth prior to damaging or removing enamel from the surface of said tooth.

19. An orthodontic bracket having a bonding base for attachment to a tooth, said bonding base having a substantially monolayer of adjacent particles secured thereto, said particles being of substantially uniform size such that small particles do not completely fill the voids between the adjacent particles, said bracket having means for allowing detachment of said bracket from said tooth prior to damaging or removing enamel from the surface of said tooth, said means comprises an adhesive bond between said particles and said bonding base such that said bond between said particles and bonding base will fail prior to failure of the bond between said particles and said tooth.

20. An orthodontic bracket according to claim 19 wherein said particles are substantially hollow spheres.

21. An orthodontic bracket having a bonding base for attachment to the surface of a tooth, said bonding base having means for minimizing removal of enamel from the tooth during removal of the bonded bracket from the tooth, said means for minimizing removal of enamel from the tooth during removal of the bonded bracket from the tooth comprises a first sealed adhesive layer secured to the base portion of the bonding base, a second intermediate layer secured to said first adhesive and a third adhesive layer bonded to the other side of said intermediate layer and to said tooth, said third adhesive layer having a bond strength greater than said intermediate layer.

22. An orthodontic bracket according to claim 21 wherein said means for minimizing removal of enamel from the tooth comprises a first adhesive layer secured to said bonding base, a second adhesive layer secured to said tooth and a third intermediate film layer made of a plastic material which is secured to said adhesive on said bonding base and said adhesive on said tooth.

23. A method of adhering an orthodontic bracket to a tooth for forming a predetermined fracture plan between an orthodontic bracket bonded to a tooth comprising the steps of:
   (a) providing an orthodontic bracket having a bonding base for attachment to the tooth;
   (b) applying a first adhesive layer to said bonding base;
   (c) providing a second, intermediate adhesive layer adjacent said first adhesive layer;
   (d) providing a third adhesive layer on the other side of said second, intermediate adhesive layer so as to sandwich said intermediate layer between said first and third layers, said third adhesive layer being secured to a tooth, said second intermediate adhesive layer having a bond strength less than the bond strength between said third adhesive layer and said tooth.

24. A method of adhering an orthodontic bracket to a tooth so as to provide a predetermined fracture plane away from said tooth adhesive bond surface comprising the steps of:
   (a) placing a first adhesive layer on the base of an orthodontic bracket;
   (b) placing a second adhesive layer on said tooth surface, partially curing said first and second adhesive layers;
   (c) providing an intermediate sealant layer on either said tooth or bracket;
   (d) placing said orthodontic bracket on said tooth.

* * * * *

UNITED STATES PATENT AND TRADEMARK OFFICE
CERTIFICATE OF CORRECTION

PATENT NO. : 5,219,283
DATED : June 15, 1993
INVENTOR(S) : Farrokh Farzin-Nia et al.

It is certified that error appears in the above-indentified patent and that said Letters Patent is hereby corrected as shown below:

Column 4, line 48, insert --20-- after "spheres" and before "applied".

Column 9, line 23, "bending" should be --bonding--.

Signed and Sealed this

Fifth Day of July, 1994

Attest:

BRUCE LEHMAN

*Attesting Officer*   *Commissioner of Patents and Trademarks*